(12) United States Patent
Zolentroff

(10) Patent No.: US 11,510,898 B2
(45) Date of Patent: *Nov. 29, 2022

(54) LIMITED RELEASE LINGUAL THIOCTIC ACID DELIVERY SYSTEMS

(71) Applicant: Molecular Product Management LLC, New York, NY (US)

(72) Inventor: William C. Zolentroff, New York, NY (US)

(73) Assignee: Molecular Product Management LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/261,444

(22) Filed: Jan. 29, 2019

(65) Prior Publication Data

US 2019/0151285 A1    May 23, 2019

Related U.S. Application Data

(63) Continuation of application No. 16/102,711, filed on Aug. 13, 2018, now abandoned, which is a continuation of application No. 15/050,462, filed on Feb. 22, 2016, now abandoned.

(51) Int. Cl.
*A61K 31/381* (2006.01)
*A61K 9/00* (2006.01)
*A61K 9/20* (2006.01)
*A61K 31/385* (2006.01)
*A61K 45/06* (2006.01)

(52) U.S. Cl.
CPC .......... *A61K 31/381* (2013.01); *A61K 9/0056* (2013.01); *A61K 9/2018* (2013.01); *A61K 31/385* (2013.01); *A61K 45/06* (2013.01)

(58) Field of Classification Search
CPC .. A61K 9/0056; A61K 9/2018; A61K 31/381; A61K 31/385; A61K 45/06
USPC ........................................................ 424/48
See application file for complete search history.

(56) References Cited

U.S. PATENT DOCUMENTS

| | | |
|---|---|---|
| 6,271,254 B1 | 8/2001 | Ulrich |
| 6,620,425 B1 | 9/2003 | Gardiner |
| 7,858,655 B2 | 12/2010 | Roehnert |
| 9,265,753 B2 | 2/2016 | Benjamin et al. |
| 2004/0026537 A1 | 2/2004 | Boecking |
| 2007/0190114 A1 | 8/2007 | Smart |
| 2007/0196442 A1 | 8/2007 | Heuer |
| 2008/0095741 A1 | 4/2008 | Wessel |
| 2009/0004281 A1 | 1/2009 | Tien |
| 2009/0104171 A1 | 4/2009 | Pardee |
| 2013/0136703 A1* | 5/2013 | Benjamin, Jr. ...... A61K 31/385 424/48 |
| 2020/0246270 A1 | 8/2020 | Bauer |
| 2021/0069117 A1 | 3/2021 | Kiran |

FOREIGN PATENT DOCUMENTS

| | | |
|---|---|---|
| CA | 2135535 | 3/2006 |
| DE | 20207569 | 12/2002 |
| DE | 20040010021 | 8/2004 |
| EP | 0654484 | 5/1995 |
| JP | 2006219467 | 8/2006 |
| KR | 20070110729 | 11/2007 |
| WO | 2009001362 | 12/2008 |
| WO | 2010127297 | 11/2010 |
| WO | 2013115736 | 8/2013 |

OTHER PUBLICATIONS

Benjamin, ALA Taste Burning Comparison Data (from 15 respondants on a 1-5 scale).
Benjamin, "The Oral Irritation or Burining due to ALA Concentrations in Buccal Applications", dated Jul. 23, 2015.
Kallai, et al., "Evaluationof Drug Release from Coated Pellets Based on Isomalt, Sugar and Microcrystalline Cullulose Inert Cores", AAPS PharmSciTech, vol. 11, No. 1, Mar. 2010, pp. 383-391.
Mauldin, "The Benefits of Alpha Lipoic Acid", Mar. 24, 2012.
Mclldulf, et al., "Critical Appraisal of the use of Alpha Lipoic Acid (thiocticacid) in the Treatment of Symptomatic Diabetic Polyneuropathy", Therapeutics and Clinical Risk Management, Sep. 5, 2011, pp. 377-385.
Mijnhout, et al., "Alpha Lipoic Acid for Symptomatic Periperal Neuropathy in Patients with Diabetes: A Meta-Analysis of Randomized Controlled Trials", International Journal of Endocrinology, vol. 2012, Article ID 456279, 8 pages.
Shay, et al., "Alpha-lipoic Acid as a Dietary Supplement: Molecular Mechanisms and Therapeutic Potential", Biochim Biophs Acta. Oct. 2009, 1790(10): 1149-1160.
Zieglar, et al., "Treatment of Symptomatic Diabetic Polyneropathy with the Antioxidant Alpha-Lipoic Acid 7-month Multicenter Randomized Controlled Trial (ALADIN III Study). ALADIN III Study Group. Alpha-Lipoic Acid in Diabetic Neuropathy", Diabetics Car 22(8) 1296-301, Sep. 1999.
Non-Final Office Action issued to U.S. Appl. No. 1550462 dated Oct. 2, 2017.
International Search Report for PCT/US2012/053557 dated Jan. 24, 2013.
International Written Option based on PCT/US2017/053845 dated Jan. 30, 2018.

(Continued)

*Primary Examiner* — Adam C Milligan
(74) *Attorney, Agent, or Firm* — Transformative Legal LLC; Len S. Smith; Denise M. Brown

(57) ABSTRACT

The invention provides new methods of treating patients benefiting from increased blood levels of alpha-lipoic acid. Such patients may include those suffering from various physiological disorders such as diabetic neuropathy. A dissolvable tablet, not meant to be swallowed, comprising alpha-lipoic acid in a limited release matrix provides means of administering therapeutically beneficial concentrations of alpha-lipoic acid without the commonly associated oral burn. Due to its orally dissolvable nature, this rate limiting matrix can deliver approximately IV-equivalent plasma levels of thioctic acid.

13 Claims, No Drawings

(56) References Cited

OTHER PUBLICATIONS

European Search Report based on PCT/US2012/053557 dated Dec. 23, 2014.
Indian Office Action based on PCT/US2012/053357 dated Apr. 9, 2018.
European Search Opinion based on PCT/US2012/053357 dated Dec. 23, 2014.
Laffleur, et al., "Advances in Drug Delivery Systems: Work in progress still needed?" Elsevier 2019, https://doi.org/10.1016/j.ijpx.2020.100050.
Bala, et al., "Orally Dissolving Strips: A New Approach to Oral Drug Delivery System", International Journal of Pharmaceutical Investigation, Apr. 2013, vol. 3, Issue 2.
Prajapati, et al., "Formulation Design Approach to Avoid Dose Domping", Pharmaceutics and Pharmaceutical Technology, S.K. Patel College of Pharmaceutical Education & Research (2008; undated in print copy).
Bankar, et al., "A Review on Orodispersible Tablets Prepared Using Spray Dried Sustained Release Microparticles", Journal of Advanced Drug Delivery 2014; 1(2); 82-95.
Syed, et al., "Recent Research in Pharmaceutical Sciences", vol. 1, Galgotias University, Weser Books, No. 79737, 2021 (edited by Sharma).
Gupta, et al., "Orodispersible Tablets: An Overview of Formulation and Technology", World Journal of Pharmacy and Pharmaceutical Sciences, vol. 9, Issue 10, 1406-1418 (2020).
Thomas, Felicity, "Taking a Controlled Approach", Pharmaceutical Technology, Jul. 2, 2020, vol. 44, Issue 7, pp. 26-29.
Bhowmik, et al., "Tablet Manufacturing Process and Defects of Tablets", Elixer Pharmacy, 70 (2014) 24368-24374.
Maderuelo, et al., "Critical Factors in the Release of Drugs from Sustained Release Hydrophilic Matrices", Journal of Controlled Release, vol. 154, Issue 1, Aug. 25, 2011, pp. 2-19.
Uddin, "Advanced Drug Delivery Systems" available via slideshare at slideshare.net/JalalUddin10/advanced-drug-delivery-system.
Garbacz, et al., "Dissolution of Mesalazine Modified Release Tablets Under Standard and Bio-Relevant Test Conditions", Journal of Pharmacy and Pharmacology, Feb. 2015; 67(2): 199-208.
Krajacic, et al., "Matrix Formulation in Sustained Release Tablets: Possible Mechanism of Dose Dumping", International Journal of Pharmaceutics, Jan. 30, 2003; 251 (2-2):67-78.
Hannan, et al., "Oral Dispersible System: A New Approach in Drug Delivery System", Indian Journal of Pharmaceutical Sciences, Jan.-Feb. 2016; 78(1):2-7.
Drug Development & Delivery, "Controlled Release Leveraging Precision Particle Fabrication® Technology to Create Patient-Friendly Dosage Forms," Web Article May 2017.

\* cited by examiner

LIMITED RELEASE LINGUAL THIOCTIC ACID DELIVERY SYSTEMS

CROSS-REFERENCE TO RELATED APPLICATIONS

The present Application is a continuation of application Ser. No. 16/102,711, filed Aug. 13, 2018, which was a continuation of application Ser. No. 15/050,462, filed Feb. 22, 2016, each of which are hereby incorporated by reference in their entirety.

BACKGROUND OF THE INVENTION

1. Field of the Invention

The present invention relates to limited release lingual/sublingual delivery systems for thioctic acid.

Thioctic acid is also known as lipoic acid, alpha lipoic acid, or ALA. Thioctic acid has two chiral enantiomers. It is found as R-(+)-lipoic acid (RLA) and S-(−)-lipoic acid (SLA), and a racemic mixture of the two R/S-Lipoic acids. Additionally, each of these thioctic acid enantiomers exist in reduced (dihydro-lipoic acid) and oxidized forms. The limited release lingual/sublingual delivery system of this disclosure is effective for any and all of the above thioctic acid variants. The term thioctic acid, alpha lipoic acid, or ALA refers to all of these various species of lipoic acid, unless specifically referred to otherwise.

The term of thioctic acid is more common in Europe. Alpha lipoic acid or ALA is more common in the United States. The scientific literature uses all these terms and therefore we will use thioctic acid, alpha lipoic acid or ALA interchangeably.

Lingual/Sublingual—Oral Mucosal Transmission

We clarify our use of "lingual" or "lingual/sublingual" as follows. Typically, lingual refers to the tongue while sublingual refers to the tissues below the tongue and the underside of the tongue. Buccal generally refer to the cheeks. Oral refers to the entire mouth; however it can also mean a pill, or the like, that is swallowed rather than dissolved in the mouth. Conversely, we believe most people understand "lingual" or "lingual/sublingual" to be something that is dissolved orally rather than swallowed intact. Another way to say this is, the ALA is transferred from the oral cavity to the body's blood stream by buccal, lingual and sublingual absorption; or the ALA is buccally, lingually and sublingually delivered. Therefore, unless specified otherwise, we use of the terms "lingual" or "lingual/sublingual" or "buccal/lingual/sublingual" to refer to a formulation dissolving in any part(s) of the entire mouth and that the active or key ingredient(s), i.e. ALA, enters the general bloodstream through various or multiple oral tissues rather than being limited to any particular portion or tissue of the mouth. We intend the following terms to have the same meaning as "lingual" or "lingual/sublingual" or "buccal/lingual/sublingual": lingual absorption, lingually delivered; Oral Mucosal Delivery, Oral Mucosal Transmission, Oral Mucosal Administration; Oral Epithelial Delivery, Transmission or Administration; and Oral Dissolution & Transmission (Oral D&T).

2. Description of the Related Art

Thioctic acid is believed to be beneficial in several applications, such as preventing organ dysfunction, the treatment of various neuropathies and polyneuropathies, and use as an antioxidant. Thioctic acid has been primarily administered by two methods in the prior art.

High Absorption Rate and High Plasma Levels/Blood Stream

First, it has been administered via intravenous (IV) therapy. In IV therapy, a solution containing thioctic acid is delivered through an IV needle directly to a patient's blood stream. This method shows the benefits of a high absorption rate and high plasma levels.

IV therapy becomes problematic, however, when the therapy is designed for use in the long-term care of a patient. In order to utilize IV therapy as a delivery system, the IV must be administered by a medical professional. This typically requires the patient to visit a healthcare provider's office or hospital each time the thioctic acid is to be administered. The time required to visit the office frequently discourages the patient from continuing these visits. Thus, the patient will often discontinue treatment due to the inconvenience of making trips to the provider's office. The necessity for treatment through an office or hospital also creates a high cost for patients, insurance companies, and researchers who want to perform clinical trials. Furthermore, in the event that the patient continues treatment, frequent IV use may cause vein collapse and oxidative stress in the patient.

The second method typically utilizes an orally administered, GI delivery system using a tablet, powder, or soft-gel formulation of thioctic acid. This offers a method of administration which does not require a health care provider's oversight. However, tablets and powders of thioctic acid are difficult for the human body to absorb.

Refined thioctic acid is insoluble in water at normal pH and at the acid pH seen in the stomach, although it is soluble in fat solvents. The dl-form of thioctic acid is likewise insoluble in water and soluble in fat solvents, but it can form a water-soluble sodium salt that is aqueous in water solutions that exist at a pH of about 7.4. However, this sodium salt also has a poor solubility at acid pH.

Due to this solubilization problem, thioctic acid taken in tablet and powder forms is almost entirely dependent upon bile salts in the small intestine for dispersal, which results in a slow absorption rate and low systemic plasma levels. Once bile salt dispersal of thioctic acid crystals has occurred, thioctic acid can penetrate epithelium in the manner of fat-soluble drugs, as well as utilize absorption mechanisms in the small intestine specific to medium chain fatty acids. Soft-gel variations of solubilized thioctic acid, and oral liquid solutions, have been developed to speed up the dispersal process. However, for the most part these solutions are prone to polymerization and degradation reactions and are unstable during long term storage. More significantly, all previous oral delivery systems (including soft-gels and oral solutions) utilize the stomach and gastrointestinal (GI) tract for absorption.

Since the liver is the major organ implicated in the removal of thioctic acid from plasma, with a removal rate nearly equal to that of the clearance of plasma through the liver, slow GI absorption rates result in low systemic plasma levels due to the necessary passage of ingested substances through the hepatic portal vein of the liver (the first pass mechanism).

To clarify, by GI absorption we mean the absorption of ALA by the GI tract, then ALA's transmission to the bloodstream via the hepatic portal vein, and then finally the ALA's entering the body's general bloodstream where ALA can be subsequently measured in the systemic blood plasma. In contrast, the absorption directly, and only, by the GI tract tissues without further transmission to the bloodstream will be referred to as GI Assimilation.

Due to the insoluble nature of thioctic acid and/or the liver's function to remove it from both systemically circulating plasma and the first pass mechanism of the hepatic portal vein, oral delivery systems that utilize the stomach and small intestine for absorption necessarily equate to relatively low absorption profiles, such that only a small percent of a given dose actually becomes utilized by the body. Therefore, a large degree of waste occurs when GI absorption mechanisms are utilized, and thus maximal benefits from thioctic acid supplementation are not achieved through GI absorption mechanisms.

Previous attempts to overcome the low absorption profiles of oral thioctic acid doses have produced their own problems and side-effects. When high concentrations of thioctic acid make continued contact with cells in the mouth and GI tract (including the stomach), those cells may swell and burst, causing an apoptotic "burn" effect. This apoptotic effect is what caused lethality in animals utilized for LD50 studies, where said animals died from liver failure. Upon histological examination, liver mitochondria of said animals were seen to have burst due to an osmotic imbalance as thioctic acid flooded into these cells. As such, due to this osmotic/apoptotic effect, current formulations of a swallowed tablet, powder, or soft-gel can be uncomfortable or harmful to the patient, particularly when taken in high enough doses to produce IV equivalent plasma levels.

An alternative solution is needed to address one or more of these shortcomings in the prior art.

BRIEF SUMMARY OF THE INVENTION

A limited release lingual/sublingual delivery system for thioctic acid is provided.

A diffusion-limiting binding agent, either hard or soft, in the lingual/sublingual formulations may include, but is not limited to: sucrose, isomalt, dextrose, lactitol, sorbitol, maltose and chicle.

The limited-release lingual/sublingual delivery system may be a lozenge, caramel, gum, or other release-limiting matrix formulation placed in the patient's mouth that that is intended to remain in the mouth. That is, the patient is not encouraged to swallow the delivery system. The formulation contains a concentration of thioctic acid between 1% and 25% by mass, preferably at a concentration of approximately 2% by mass.

Individual lozenges, candies, or other lingual delivery systems are expected to be from 1.0 g to 30.0 g, with thioctic acid dose variations from 10 mg to 600 mg. However, extremely low-dose variations (from 5.0 mg to 10 mg) of thioctic acid are anticipated, such that lozenges for general consumption as a supplement are also included, in addition to the high-dose formulations intended for specific therapeutic effects. These therapeutic applications may include the treatment of Alzheimer's, Diabetic peripheral neuropathies, retinal neuropathies, and other physiological states where thioctic acid therapy is advised or under investigation.

DETAILED DESCRIPTION OF THE INVENTION

Through the course of study, while inventing the first marketed form of solubilized thioctic acid (ThioGel.TM.), the inventor of this limited-release lingual/sublingual delivery system noted that solubilized forms of thioctic acid, be they in aqueous solutions or in fat solvents, are able to pass through the epithelium of the mouth and GI tract due to the dispersed nature of the molecules. However, initial attempts to utilize lingual absorption mechanisms resulted in a burn effect that was revealed to be equivalent to the apoptotic effect observed in the livers of animals utilized for LD50 studies.

To be clear, not every substance can pass through the epithelium of the mouth (oral epithelium). It is well known that a substance can be administered lingually, i.e. dissolved in the mouth, but that does not mean that the substance will pass through the oral epithelium and into the bloodstream. Therefore, some substances, nutraceuticals or drugs can be effectively administered lingually, and some cannot. In the case of ALA, it was not obvious or expected that it could be administered lingually, i.e. pass through the oral epithelium. That ALA could be delivered through the oral epithelium was the first discovery made by the primary inventor.

As noted in a later paragraph: "Not all lingual/sublingual delivery systems are effective. Instead, the act of swallowing leads to GI absorption as the primary route of absorption." By this, we mean that a substance that is dissolved in the mouth, but cannot be absorbed through the oral epithelium, may appear to be lingually delivered, but it is not. The absorption is actually occurring through the digestive tract after the substance has dissolved in the mouth and been swallowed (and is therefore typically less effective).

However, as mentioned, the lingual absorption of ALA, i.e. high concentrations of ALA for relatively extended periods of time in the oral cavity (as opposed to swallowing as the primary method of delivery), has a negative side effect of oral burning or oral irritation and a somewhat unpleasant flavor.

The present limited-release invention addresses these negative effects through the use of sucrose-based and non-sucrose-based candies, gums, and lozenges in various concentration and flavor combinations. A flavored lingual/sublingual delivery system in the concentration range of 1%-6% thioctic acid (by mass), not only removes and/or minimizes these effects, but it also improves the palatability of the raw compound (thioctic acid).

Provided that the lingual/sublingual delivery system is homogeneous, and the thioctic acid concentration is within the preferred range, the release of thioctic acid onto lingual surfaces is delayed and dispersed enough that the burn effect is overcome, especially within the concentration range of 1-3% thioctic acid (by mass). This means an 11-gram lozenge, candy, gum, or other lingual delivery system can be utilized to deliver 200 mg of thioctic acid without noticeable negative effects. Slightly greater concentrations of thioctic acid (up to the 6% range) can also be utilized without excessive negative effects; however, as the concentration increases so too does the burn effect.

To confirm, objectify, and increase the precision of our individual findings on acceptable concentration levels of ALA in a lozenge, we performed a study titled "The Oral Irritation or Burning due to ALA Concentrations in Buccal Applications" (Acceptability Study). We disclosed our test and data to the USPTO in connection with the prosecution of our U.S. patent application Ser. No. 13/602,093. In this test, we provided ALA lozenges in three concentrations: 3%, 6% and 9% ALA (by weight). These hard candy sugar lozenges were cinnamon flavored and weighed approximately 3 grams each. The lozenges had an asymmetric, shallow, essentially hemispherical shape, comprised of a 1-inch diameter circle on one side and a 0.3 inches deep hemisphere on the other side (the two sides meeting at the perimeter of the 1-inch diameter circle). The surface area of these lozenges was approximately the same surface area as a 6 g spherical lozenge. We say essentially hemispherical, because the mold that formed the lozenges is actually a polygon whose flat facets approximate a hemisphere. The surface area of these lozenges is approximately 1.8 in$^2$.

Our findings were that the 3% ALA lozenge was acceptable, on average, for 85% of our 15-person test population. The 6% in ALA lozenge scores were neutral (i.e. a balance between acceptable and unacceptable). The 9% ALA lozenge was, on average, 78% unacceptable.

Our findings provide a useful baseline of information to determine the concentration of ALA acceptable for fairly typical lozenge in a lingual application.

Having established that higher concentrations of thioctic acid in a lozenge or other lingual delivery systems increase the negative side effects, we must now consider the limitations of that data. While there is a direct correlation, this assumption only holds true when the lingual delivery system and its matrix remain constant, i.e. the assumption is an oversimplification. It cannot be assumed that all lingual delivery systems and their matrixes will dissolve at the same rate as each other. Additionally, increased surface area will increase the rate of ALA delivery to the saliva. Therefore, we provide greater specificity of not only defining or limiting the range of ALA concentration in the lingual delivery system, but also defining and limiting the range(s) of the rate of ALA release from the lingual delivery system into the oral cavity. To link acceptable, neutral and unacceptable concentrations of ALA to ALA release rates, we first establish a baseline based on user data.

An in situ Oral Dissolution Trial used a 3% ALA, hard candy sugar lozenge having the same shallow hemispherical shape as the Acceptability Study lozenge, hence a similar surface area. The lozenge was placed in the mouth for one minute, taken out and weighed (for 30 seconds) and returned to the mouth. This process was repeated until the lozenge fully dissolved in up to 10 minutes. The average trial weight of the lozenges was 3.64 g. The average Peak ALA Release Rate (also the average maximum ALA Release Rate) was 20.18 mg/min (column 7, titled "Release Rate (mg/min)") which occurred between the one- and two-minute marks. See the detailed chart below.

TABLE 1

In situ Oral Dissolution Trial Results (3.43 g Ave, 3% ALA, hard candy sugar lozenge)

| Time (min) | Weight (g) | Change Weight (g) | % ALA | mg ALA lost | mg ALA in Solution | Release Rate (mg/min) |
|---|---|---|---|---|---|---|
| 0 | 3.43 | 0 | 3 | 0 | 0.00 | 0.00 |
| 1 | 3.43 | 0.59 | 3 | 17.63 | 17.63 | 17.63 |
| 2 | 2.84 | 0.67 | 3 | 20.18 | 37.80 | 20.18 |
| 3 | 2.17 | 0.55 | 3 | 16.58 | 54.38 | 16.58 |
| 4 | 1.62 | 0.49 | 3 | 14.70 | 69.08 | 14.70 |
| 5 | 1.13 | 0.46 | 3 | 13.65 | 82.73 | 13.65 |
| 6 | 0.67 | 0.32 | 3 | 9.53 | 92.25 | 9.53 |
| 7 | 0.36 | 0.21 | 3 | 6.15 | 98.40 | 6.15 |
| 8 | 0.15 | 0.10 | 3 | 3.08 | 101.48 | 3.08 |
| 9 | 0.05 | 0.05 | 3 | 1.43 | 102.90 | 1.43 |

As seen in column 7 of the Oral Dissolution chart, the first minute of dissolution (17.63 mg/min) does not provide highest ALA release rate. We believe this is due to the time required for a softening process of the outer portion of matrix by the saliva prior to actual dissolution. In the second minute of dissolution, the Peak ALA Release Rate is reached at 20.18 mg/min. In the third minute of dissolution, the rate drops to 16.58 mg/min and continues to descend in the subsequent minutes. Presumably, this is due to the decreasing surface area of the lozenge as it becomes smaller.

We note that the data from an individual lozenge did not always follow the exact progression of the averages. The first or third minute could produce a higher ALA Release Rate than the second minute of dissolution. This points to the issue that the amount of saliva, motion, abrasion and physiological differences that naturally occurs in the mouth when sucking on a lozenge varies from person to person and, even with the same person, from instance to instance. We will address this issue towards the end of our disclosure by providing two methods of ex vivo ALA Release Rate measurement utilizing (1) a USPC Type 2 Paddle Apparatus or (2) a USPC Type 4 Flow-Through Cell Apparatus.

Note, column 6, titled "mg ALA in Solution" in the above Oral Dissolution Trial chart, is not actually relevant to the in-situ method of measurement. It really reflects an ex vivo test where the ALA is not being removed from the saliva. In actual use, in situ, the ALA is (1) being removed from the saliva via the oral tissues and (2) being removed along with saliva from the oral cavity by swallowing. If real time measurement of ALA in the saliva were possible, a more complex and nuanced picture would likely emerge. However, it's reasonable to assume that that picture would still generally reflect, and correlate with, the ALA Release Rates of column 7.

Linking the concentration of ALA in the lozenge to its Peak ALA Release Rate proceeds as follows. A 3% lozenge has a Peak Release Rate of 20 mg/min; a 6% lozenge has a peak of 40 mg/min; and a 9% lozenge has a peak of 60 mg/min.

Accordingly, the Acceptability Study ALA percentages of 3%, 6% and 9% which had an acceptability rating of acceptable, neutral and unacceptable, correlate to a Peak ALA Release Rates of 20 mg/min that is acceptable, 40 mg/min that is neutral, and 60 mg/min that is unacceptable.

However, the issue of acceptability is actually more complex. The degree to which negative effects are considered excessive depends not only on the ALA concentration in the lozenge, the ALA Release Rate and resulting ALA levels in the saliva, but also on the context in which the ALA is being administered.

When a supplement or drug has side effects, the degree to which they are considered acceptable depends considerably on the severity of the problem being alleviated. The acceptable negative side effects of chemotherapy to treat cancer would not be acceptable for a vitamin being taken as a supplement. Meanwhile, the range of applications for thioctic acid is quite broad, ranging from an antioxidant health supplement, to a diabetic neuropathy treatment (reduction of pain and other symptoms), and even extends to a treatment for life-threatening mushroom poisoning. Clearly, the ranges of acceptable negative side effects related to lingual ALA delivery (e.g. oral burning/irritation) depend on the particular application.

To provide greater specificity on this issue, we have identified five levels of acceptability ranging from Agreeable to Tolerable. The levels proceed from lower amounts of side effect (that are considered acceptable) to higher. Each level is divided into two subcategories, a and b, respectively representing everyday use and occasional (or intermittent) use. Level b would generally be expected to have a higher threshold of acceptable negative side effects than level a, because the user would experience the side effects less often. The categories are detailed as follows.

Level-1a is Agreeable for everyday prophylactic or supplemental use to promote health and for occasional use is level-1b. That is to say, Level-1a represents an Agreeable response by the average user to a relatively low threshold of acceptable negative side effects in everyday use.

Level-1b represents a presumed higher threshold of acceptable negative side effects due to less frequent use.

Level-2a is Satisfactory for everyday use to mitigate or treat a health problem or disease and for occasional use the level is 2b.

Level-3a is Adequate for everyday use to reduce pain and for occasional use the level is 3b.

Level-4a is Preferable to IV for everyday use and for occasional use the level is 4b.

Level-5a is Tolerable for everyday use to improve very severe, or life-threatening, medical conditions and for occasional use the level is 5b. That is to say, Level-5a represents a Tolerable response, on average, to a high threshold of acceptable negative side effects in everyday use. Level-5b represents the highest threshold of acceptable negative side effects of all Levels, because the use is occasional.

To reiterate, the maximum level of ALA concentration and consequent side effects that is acceptable at Level-5b is generally not acceptable at Level-5a or the lower levels 4-1. The maximum level of ALA concentration and consequent side effects that is acceptable at Level-4 is generally not acceptable at Levels-3 or below, and so on.

The exact order of these levels, particularly level-4 "Preferable to IV", may be different or altered based on feedback from subject use and tests.

Minor note: the maximum daily concentration and consequent negative side effect threshold would likely be unique for each Level, but we would expect overlap below the maximum levels. For example, if a lozenge with a concentration of 1-3% ALA (and its resulting oral irritation) are acceptable for Level-1a and a lozenge with a concentration of 1-15% ALA is acceptable for Level-5b, then there is an overlap between the two Levels in the 1-3% range.

Also, particular applications might span multiple Levels. For example, Levels 2, 3 and 4 could apply to diabetic neuropathy. And Levels 3, 4 and 5 could apply to later stages of diabetic neuropathy. The resulting lexicon for referencing levels of acceptability may be utilized as follows: Agreeable-1, Satisfactory-2, Adequate-3, Preferable-4, Tolerable-5. To specify sub level, denotation as follows: Agreeable-1a (or -1b), Satisfactory-2a (or -2b), Adequate-3a (or -3b), Preferable-4a (or -4b), Tolerable-5a (or -5b). Also, either Level or the adjective name may be used interchangeably, e.g. Level-1 is the same as Agreeable-1.

A unique one-word adjective is also used to describe each Level, but when referring specifically to each Level by name it will be followed by a hyphen, the level number and, when distinguishing between daily and occasional use, the sub level letter a or b, as follows: Agreeable-1, Satisfactory-2, Adequate-3, Preferable-4, Tolerable-5. To specify sub level, denotation as follows: Agreeable-1a (or -1b), Satisfactory-2a (or -2b), Adequate-3a (or -3b), Preferable-4a (or -4b), Tolerable-5a (or -5b). Also, either Level or the adjective name may be used interchangeably, e.g. Level-1 is the same as Agreeable-1.

The next step is to connect these five Levels to the Peak ALA Release Rates. Based on our informal use, we would approximately correlate Agreeable-1 to the 20 mg/min rate; Acceptable-2 to 40 mg/min rate, and Adequate-3 or possibly Preferable-4 to 60 mg/min. We believe the acceptable side effects for Level Tolerable-5, particularly Tolerable-5b, exceeds the maximum 9% ALA concentration (and Peak ALA Release Rates of 60 mg/min) from the Acceptability Study. They may correspond to something closer to a 12% ALA concentration and 90 mg/min Peak ALA Release Rate.

However, more studies and test data are needed to truly define the contextual acceptability of Peak ALA Release Rates in relation to the five Levels. It's conceivable that a rate twice as high as the 60 mg/min Peak ALA Release Rate would be considered tolerable by users at the Tolerable-5b level. Accordingly, we furnish below Table 2 (in two parts, a first portion column 1 through column 10 and a second portion column 11 through column 18) to provide expected and/or possible Peak ALA Release Rates that we expect to find after more acceptability testing using the five different Levels of acceptability.

The below Table 2 starts with a range of ALA matrix concentration ("Matrix Conc.") and ALA Release Rates ("Rate mg/min") (based on the initial Acceptability Study) in columns 1 and on the left (these first two columns are also repeated in the continued table). The next two columns, 3 and 4, show what the ALA concentration and release rates are when increased by 110%. The successive columns continue to multiply the initial ranges (columns 1 and 2) by increasingly larger percentages, up to 200% in in columns 15 and 16.

The last two columns, 17 and 18, show only ALA matrix concentrations. The reason for this is that ALA concentrations could be more than twice the original amounts without increasing the Release Rates by the same ratio. That is because the rate at which the matrix dissolves could be slowed considerably by a variety of ingredients (as will be noted later). Therefore, a lozenge or other lingual delivery system can be made with a relatively higher concentration of ALA and still have a relatively lower ALA Release Rate.

TABLE 2

Maximum Acceptable ALA Matrix Concentrations and ALA Release Rates

| 1 | 2 | 3 | 4 | 5 | 6 | 7 | 8 | 9 | 10 |
|---|---|---|---|---|---|---|---|---|---|
| Matrix Conc. | Rate mg/min | Conc. 110% | Rate 110% | Conc. 120% | Rate 120% | Conc. 130% | Rate 130% | Conc. 140% | Rate 140% |
| 1% | 6.67 | 1.10% | 7.33 | 1.20% | 8.00 | 1.30% | 8.67 | 1.40% | 9.33 |
| 2% | 13.33 | 2.20% | 14.67 | 2.40% | 16.00 | 2.60% | 17.33 | 2.80% | 18.67 |
| 3% | 20.00 | 3.30% | 22.00 | 3.60% | 24.00 | 3.90% | 26.00 | 4.20% | 28.00 |
| 6% | 40.00 | 6.60% | 44.00 | 7.20% | 48.00 | 7.80% | 52.00 | 8.40% | 56.00 |
| 9% | 60.00 | 9.90% | 66.00 | 10.80% | 72.00 | 11.70% | 78.00 | 12.60% | 84.00 |

TABLE 2-continued

Maximum Acceptable ALA Matrix Concentrations and ALA Release Rates

| 1 Matrix Conc. | 2 Rate mg/min | 11 Conc. 150% | 12 Rate 150% | 13 Conc. 175% | 14 Rate 175% | 15 Conc. 200% | 16 Rate 200% | 17 Conc. 250% | 18 Rate 300% |
|---|---|---|---|---|---|---|---|---|---|
| 1% | 6.67 | 1.50% | 10.00 | 1.75% | 11.67 | 2.00% | 13.33 | 2.50% | 3.00% |
| 2% | 13.33 | 3.00% | 20.00 | 3.50% | 23.33 | 4.00% | 26.67 | 5.00% | 6.00% |
| 3% | 20.00 | 4.50% | 30.00 | 5.25% | 35.00 | 6.00% | 40.00 | 7.50% | 9.00% |
| 6% | 40.00 | 9.00% | 60.00 | 10.50% | 70.00 | 12.00% | 80.00 | 15.00% | 18.00% |
| 9% | 60.00 | 13.50% | 90.00 | 15.75% | 105.00 | 18.00% | 120.00 | 22.50% | 27.00% |

Having increased the specificity, and potential specificity, of the maximum ALA Matrix Concentration and ALA Release Rates, we now similarly consider their minimums.

At some point, the amount of ALA delivered to a person's bloodstream can become too small to be meaningful, typical or measurable. Generally, the amount that is prophylactically useful as a supplement is smaller than the amount required for the treatment of a disease. Beyond that, to determine a minimum ALA Matrix Concentration, we must consider the relationship between concentration and the dose received.

A low ALA Matrix Concentration could still provide an effective amount of ALA. For example, 0.25% ALA Matrix Concentration delivered by the previously mentioned 11 g lozenge would still provide a dose of 27.5 mg of ALA. Because so much more lingual ALA enters the general bloodstream than ingested ALA, this dose is approximately equivalent to 100 mg of ingested ALA. 100 mg pills of ALA are quite typical in the current market. This would suggest a dose that is half of that may still be serviceable; therefore a 0.125% ALA Matrix Concentration may be a valid dose, particularly when used as a supplement. Because some amount of experimentation would be required to zero in on the exact amount, we have outlined minimum balance of ALA Matrix concentrations and their related ALA Release Rates in a Table 3 formatted similarly to Table 2.

Table 3 below discloses Minimum ALA Matrix Concentrations of 0.75%, 0.50%, 0.25% and 1.25% and related ALA Release Rates. These amounts are then decreased/increased by 8% and 15% in the subsequent columns. This yields a wider range of Minimum ALA Matrix Concentrations and Minimum ALA Release Rates. Subsequent use, measurement and experimentation will help determine the relevant minimums.

The minimum dose of ALA (and related ALA Matrix Concentrations and ALA Release Rates) that can be lingually administered and provide a measurable amount of ALA in the blood stream (Minimum Measurable Blood ALA) is of particular interest, because it would be quite objective. The minimum dose of ALA that can be lingually administered and provide a meaningful supplementation of ALA is a somewhat more subjective, albeit more purposeful. Again, the minimums expected for a particular condition or disease would likely be larger than the supplementation minimums.

TABLE 3

Minimum ALA Matrix Concentrations and ALA Release Rates

| 1 Matrix Conc. | 2 Rate mg/min | 3 Conc. 92% | 4 Release 92% | 5 Conc. 108% | 6 Release 108% | 7 Conc. 85% | 8 Rate 85% | 9 Conc. 115% | 10 Rate 115% |
|---|---|---|---|---|---|---|---|---|---|
| 0.13% | 0.83 | 0.12% | 0.767 | 0.14% | 0.900 | 0.11% | 0.71 | 0.14% | 0.96 |
| 0.25% | 1.67 | 0.23% | 1.533 | 0.27% | 1.800 | 0.21% | 1.42 | 0.29% | 1.92 |
| 0.50% | 3.33 | 0.46% | 3.067 | 0.54% | 3.600 | 0.43% | 2.83 | 0.58% | 3.83 |
| 0.75% | 5.00 | 0.69% | 4.600 | 0.81% | 5.400 | 0.64% | 4.25 | 0.86% | 5.75 |

Tables 2 and 3 cover the range of ALA Matrix Concentrations and ALA Release Rates. For example, the largest ALA Matrix Concentration range among column 1 values is 0.13% from Table 3 up to 9% in Table 2. Yet the largest range of ALA Matrix Concentration anywhere, is from 0.1% in Table 3/column 7 going up to 27.00% in Table 2/column 18.

At the same time, the largest range of ALA Release Rates in column 2 is from 0.83 mg/min in Table 3 up to 60 mg/min in Table 2. Yet the largest range of ALA Release Rates anywhere is from 0.71 mg/min in Table 3/column 8 up to 120 mg/min in Table 2/column 16.

Therefore, a range of ALA Release Rates from 0.71 mg/min to 120 mg/min is a possibility, somewhat preferably ranging from 1.67 mg/min to 90 mg/min; preferably 3.33 mg/min to 60 mg/min; more preferably 5.0 mg/min to 40 mg/min; and most preferably 6.67 mg/min to 20 mg/min.

As noted earlier, the Peak ALA Release Rate occurs in the earlier portion of the ALA lozenge's dissolution and is the maximum ALA Release Rate. In the later portion of the dissolution, the lozenge's surface area decreases and reduces the ALA Release Rate. This holds true only if the user is not chewing the lozenge, because that would break it into smaller pieces (disintegration) and increase the total surface area. Depending on the degree to which the lozenge is broken up, this new surface area amount could exceed the original surface area and cause a higher Peak ALA Release Rate, thus becoming the new maximum ALA Release Rate. That in turn could potentially cause an unacceptable increase in negative side effects.

Compressed tablets, often used for lingual and/or sublingual applications, have a similar problem of breaking up into smaller pieces, particularly as they approach the end of the dissolution process. When used as an ALA formulation, this could create the problem of producing a spike in ALA release and thereby creating a second Peak ALA Release Rate that potentially exceeds the first Peak ALA Release Rate. To clarify, the first Peak ALA Release Rate results from only dissolution, while the second Peak ALA Release Rate is the result of disintegration and dissolution. However, the degree to which the tablet has already diminished in size and surface area may render the issue of disintegration moot. Restated, if the second Peak ALA Release Rate does not exceed the first Peak ALA Release Rate, then the spike of ALA release caused by the disintegration would not change the maximum ALA Release Rate and would not increase any negative side effects and therefore would not be problematic.

The terms Sustained Release and Limited Release both refer to a formulation used for the lingual administration of active ingredient(s) that are slowly dissolved in the mouth. Because a second Peak ALA Release Rate does not exceed the first Peak ALA Release Rate, we are classifying it as Sustained Release. For many active ingredients that are lingually administrated, Sustained Release is acceptable because there is no significant negative side effect to a Release Rate spike that increases the maximum Release Rate. In the case of ALA, a second Peak ALA Release Rate that increases the maximum Peak ALA Release Rate may cause negative side effects to increase from acceptable to unacceptable.

However, if the second Peak ALA Release Rate is higher than the first Peak ALA Release Rate for the same compressed tablet or ALA formulation, possible solutions are lowering the ALA concentration or increasing the matrix dissolution rate, such that the second Peak ALA Release Rate falls within acceptable parameters for the application.

Accordingly, a compressed tablet (formed by compressing the matrix ingredients rather than melting them together with heat) may be a viable option for the lingual administration of ALA. Despite the potential disintegration problems and possibly having a faster a matrix dissolution rate, the compressed tablet has the advantage of not using heat. This would allow heat-sensitive ingredients other than ALA to be incorporated in the matrix. It may also be less expensive and/or easier to manufacture, and the necessary equipment may be more accessible to some.

Returning to the hard candy lozenge as a version of the limited-release lingual formulation, a key to its creation lies in the melting points of sugar or isomalt relative to the sublimation temperature of thioctic acid. Since thioctic acid sublimates (i.e., goes from a solid to a gaseous phase without turning into a liquid or breaking down) above 160 degrees Celsius, and sucrose and isomalt formulations are commonly made below this sublimation temperature, it is possible to add thioctic acid to molten sucrose or isomalt without changing the structure of the thioctic acid itself. Thus, a wide range of natural sugar or sugar substitute-based formulations are possible. During this process, thioctic acid can be combined with the molten release limiting matrix prior to the addition of secondary flavoring compounds or after flavoring oils are added. For most other vitamins and drugs, this temperature range would pose a problem.

The lozenge (typically hard candy) and the compressed tablet constitute the most common formulations for lingual and/or sublingual administration. There are other potential formulations for lingual administration including caramels, gum, gummies (soft chewables), and liquid held in the mouth before swallowing; however, these are the not common lingual and/or sublingual formulations. Therefore, we will refer to the lozenge and compressed tablet formulations as Primary Formulations and to the remaining formulations as Secondary Formulations.

These Primary Formulations generally have a fairly simple shape, which is solid, generally thick (i.e. stocky, compact, not thin) and generally an oblong shape or a circular (or approximately circular) disk. We will call these Primary Forms. These Primary Forms have a generally low surface area to volume ratio, but not as low as a spherical shape which has the minimum surface area to volume ratio. For greater specificity, we define the Primary Forms as having a given volume 1× (a First Volume) whose surface area (a First Surface Area) is less than, or equal to, a surface area (a Second Surface Area) of a sphere whose volume (a Second Volume) is 2.2× (2.2 times as large the First Volume), wherein both forms (the Primary Form and the sphere) have the same density (typically by being comprised of the same matrix material). For example, a 4 g lozenge with a surface area to volume ratio equal to or less than an 8 g sphere (assuming identical matrix material, therefore twice the volume equaling twice the mass) is a Primary Form. In this example, the same would be true for a 5 g, 6 g, etc. lozenge; but not a 2 g or 3 g lozenge.

Other forms have larger ratios of surface area to volume, particularly shapes that are thin or elongated such as a stick of gum, convoluted shapes, or shapes with a single or multiple interior cavities, all of which we will call Secondary Forms.

To put it very simply, or in more layman-type terms, most typical lozenges and compressed tablets in current use for lingual and/or sublingual administration are Primary Formulations and have Primary Forms.

There is one Secondary Form that is of particular interest to us: the torus shape. As a hard candy, the torus shape (similar to a disk with a hole in the center) is probably best exemplified by the Lifesaver brand candy. The advantage of the torus shape for our application is that the difference between the initial surface area before dissolution and the diminishing surface area during dissolution is less pronounced.

Compared to a solid cylinder shape typical of lozenges and tablets, a torus shape with similar outside dimensions will have a larger surface area. This is not particularly beneficial, but maintaining a larger surface area during dissolution is helpful. An ideal ALA Release Rate would not have a significant peak, but rather maintain a fairly constant release rate. The torus shape could provide an ALA Release Rate that is more consistent than a simple non-torus solid disc shape.

To clarify, a torus is defined as a ring-shaped surface generated by rotating a circle around an axis that does not intersect the circle. We do not mean the definition to be quite this precise. The ring-shaped surface could be generated by rotating a circle or some other cross-section shape such as a square, square with large radii corners, or triangle, pentagon, hexagon etc., or some asymmetric variation of the shapes. Also, the rotation around the axis would not have to be circular, but could be elliptical (as viewed from above), square or some other geometric shape including those just noted above. The main point is that the otherwise solid shape as a hole through the center that allows the dissolution of the matrix on the outside surfaces (of the otherwise solid shape) as well as the "inside" surfaces defined by the hole. Using more than a single hole could also be an option, however this would increase the initial surface area even more.

Another name for our formulation, intended for Oral Dissolution & Transmission, is AlphaBon™. When the AlphaBon formulation is a lozenge, we then refer to it as an AlphaBon lozenge. When the formulation is a compressed tablet, we then refer to it as an AlphaBon tablet, and so on.

The ALA lozenges used in the in situ Oral Dissolution Trial of TABLE 1 have a surface area of approximately 1.8 in..sup.2. Given a tolerance range of about 10%, this would translate into a range of 1.6 to 2.0 in..sup.2 Given a tolerance range of about 20%, this would translate into a range of 1.4 to 2.2 $in^2$.

The ALA lozenges used in the in situ Oral Dissolution Trial of TABLE 1 have a hard candy sugar matrix whose formulation is described in the section titled "SUCROSE Based Lingual Thioctic Acid Manufacturing Process (Small Scale)". This hard candy sugar matrix will dissolve a given rate which can be determined by experimentation.

A range of ALA Dissolution Rates can be specified as an ALA formulation having a Dissolution Rate similar to a particular ALA hard candy sugar lozenge as now described. Such particular lozenge would be made by the aforementioned Sucrose Based Manufacturing Process with a surface area ranging between 1.4 and 2.2 in..sup.2, preferably between 1.6 and 2.0 in..sup.2, or most preferably 1.8 in..sup.2; and such particular lozenge ranging in ALA concentrations as described between those described in Table 3 (Columns 1, 3, 5, 7, 9) and Table 2 (Columns 1, 3, 5, 7, 9, 11, 13, 15). This range of ALA concentration would specifically include possibly from 0.11% to 18%, preferably from 0.25% to 12%, more preferably 0.50% to 9%, and most preferably 1% to 6%.

We disclose a further aspect of our limited release lingual/sublingual delivery systems for thioctic acid regarding localized ALA concentrations verses the entire oral cavity. As ALA is released from our formulation, it is inherently a higher concentration adjacent to the formulation itself as the ALA dissipates into the rest of the saliva and into other portions of the oral cavity. For this reason, we recommend moving the formulation to different parts of the mouth, particularly from cheek to cheek and underneath the tongue during dissolution to prevent excessive buildup of ALA in any single area. This is particularly relevant to any portions of oral tissue in direct contact with the formulation. The ALA is the most concentrated there because it doesn't have the space to dissipate easily. For this reason, buccal patches (or thin-film delivery systems) are unsuitable, and also because they are designed for rapid release of the active ingredient. Such release could possibly lead to sores as an apoptotic burn may occur on the inner cheek, or other oral tissues, due to the tissues' experiencing a more concentrated and more sustained ALA exposure.

We further disclose that thioctic acid is co-transported into cells along with glucose. This means that mechanisms for thioctic acid absorption exist in the buccal cavity, where sugar is readily absorbed. Therefore, unlike many lingual/sublingual vitamins and supplements, faster and more complete absorption into oral tissues of thioctic acid can occur in the mouth, because of the co-presence of sugar in the saliva. Not all lingual/sublingual delivery systems are effective. Instead, the act of swallowing leads to GI absorption as the primary route of absorption.

We are unaware of any published studies that conclusively indicate that ALA is co-transported along with glucose or fructose from the oral cavity into the bloodstream, but based on our own experience with lingual ALA lozenges, we believe this is the case. We believe that many or most natural sugars are actively transported from the saliva, through the oral membranes, and into the bloodstream. Furthermore, we believe that ALA is transported along with these sugars.

We have noticed that a given concentration of ALA in an isomalt (an artificial sugar) matrix has a stronger burning sensation compared to a similar concentration of ALA with glucose, fructose, or sucrose-based matrix. While there are other mechanisms that might explain this, we believe that glucose, fructose, or sucrose may assist in the active transport of ALA across the oral membranes. Furthermore, it may be that this occurs with other natural sugars such as monosaccharides, including galactose; disaccharides, including lactose and maltose; and possibly some oligosaccharides. We presume that this does not occur with artificial sugars, because the active transport mechanism would not recognize or be able to interact with these molecules.

There is a twofold advantage to faster transport of ALA across the oral membranes. The first is more rapid removal of ALA from saliva. This reduction of ALA concentration reduces its burning side effect. In turn, this could allow for a higher ALA Release Rates without increasing ALA concentrations in the saliva. The second advantage is that the ALA gets into the bloodstream faster, which can improve peak concentrations of ALA in the bloodstream.

These two advantages work together synergistically. If ALA moves more rapidly from saliva, then it is possible to increase the amount of ALA in the formulation, resulting in higher ALA Release Rates. Then more ALA can be released into the saliva, which in turn could further increase the rate at which ALA enters the bloodstream, which in turn increases the peak concentrations of ALA in the bloodstream. Restated, if (1) the rate-limiting step during lingual administration of ALA is the transition process from saliva through the oral membranes, to the bloodstream; and (2) glucose, fructose or natural sugars increase this step; then (3) the final goal of higher peak concentrations of ALA in the bloodstream can be achieved due to the presence of matrix such sugar. Additionally, it's easy for such sugar to be a part of the formulation. It's also a simple matter to adjust the ALA concentration of the formulation to increase or decrease its release rate.

The goal of higher peak concentrations of ALA in the bloodstream bears further discussion.

Importantly, data on the pharmacokinetics of thioctic acid in diabetes and other pathological states implies that peak plasma levels and percent utilization (based upon an area under the curve analysis) [-] may be more important than specific oral doses. Based upon this assumption, and data that shows superior peak plasma levels for limited release lingual versus GI absorption delivery systems, limited-release lingual delivery systems are expected to be more effective than GI delivery systems, Thus, IV-like beneficial effects using this limited-release lingual delivery system are actually expected to exist at a range of 300-600 mg thioctic acid, which equates to a lozenge-like formulation with a total mass of only 18-36 g. It is impossible to achieve the same IV-equivalent plasma levels in GI delivery systems without deleterious side effects associated with such high doses.

Aside from these deleterious side effects, it is not possible for GI delivery systems to achieve the high peak ALA plasma levels of IV or our limited-release lingual delivery systems, because the GI delivery is an inherently slower overall process.

One of the side effects observed during IV delivery of thioctic acid is a hypoglycemic response. For this reason, even for diabetics, glucose is commonly added to the IV mixture. This hypoglycemic response has never been reported for existing oral delivery systems. However, during initial testing of the limited-release lingual delivery system, a significant number of test subjects experienced this hypoglycemic response. Therefore, not only are IV plasma levels obtained by the limited-release lingual delivery system, but associated side effects as well. This implies the same therapeutic effects obtained during IV delivery can be expected during clinical trials.

This highlights yet another advantage of glucose, fructose, sucrose and presumably other natural sugars. Not only can they assist in the transfer of ALA from the saliva to the bloodstream and thereby reduce the negative side effects of oral burning, but they can also reduce the negative side effect of hypoglycemia once the ALA is in the bloodstream. This is a further synergy. As discussed earlier, sugar can play a role in increasing the peak concentration of ALA in the bloodstream; now we see it also can assist in the side effects from that peak concentration.

However, many diabetic patients placed under thioctic acid therapy might be uncomfortable with a sucrose-based delivery system. Therefore, a sugar-free version of the lingual delivery system was created, using isomalt in the place of sucrose. This isomalt variation shows the same basic characteristics as the sucrose formulation originally tested. That is to say, the isomalt formulations can achieve similar high peak concentrations of ALA in the bloodstream and presumably other sugar-free (i.e., sugar substitute or artificial sugar) formulations as well.

In both the sucrose and sugar-free formulations tested, the release of thioctic acid from the dispersal medium occurs slowly, as the lingual delivery formulation dissolves. Thus, thioctic acid is spread across lingual surfaces in local concentrations that remain low at any given moment. This means that the cellular burn described above is minimized, and thioctic acid can be quickly delivered to systemic circulation in doses that reach high plasma concentrations (especially in comparison to GI absorption levels) without flooding local cells.

In other words, our limited-release lingual/sublingual delivery systems for thioctic acid achieves two important objectives simultaneously. The formulation can release ALA slowly enough to prevent burning or undo irritation of the oral tissues and that the same time the ALA Release Rate is fast enough to provide high peak plasma levels in the bloodstream.

The rate at which the limited release lingual/sublingual delivery system dissolves in the mouth is not a simple matter of dissolving the matrix in water. The mouth contains specific enzymes that are designed to break down complex sugars, as well as mechanisms for the absorption of simple sugars. Accordingly, including substances that inhibit enzymic breakdown of the matrix will slow the rate of dissolution and thus affect the relative concentration in the mouth. An obvious example is the isomalt matrix itself, which contains a synthetic sugar related to sucrose which cannot be cleaved into glucose and fructose due to the inverted nature of its covalent bond. This matrix, at least theoretically, dissolves slower in the mouth than the sucrose-based matrix. Thus, the isomalt matrix itself may be a slight inhibitor of thioctic acid release.

To any of the above-mentioned formulations, the addition of specific compounds that inhibit the rate of breakdown is intended. Because there are no specific enzymes in the mouth responsible for breaking down proteins and long chain lipids, these ingredients will further limit the release of thioctic acid into the mouth, overcoming the apoptotic burn, while enabling lingual absorption mechanisms to bypass the first pass mechanism of the liver. A few specific examples include lecithin, glycine, potassium bitartrate (cream of tartar), protein hydrolysate, hydrolyzed collagen, linolenic acid, and/or other food-grade proteins and fatty acids.

As mentioned earlier, these dissolution-slowing substances would allow higher concentrations of ALA in a given formulation without increasing the ALA Release Rate. This highlights that, both in optimizing delivery and minimizing side effects, the ALA Release Rate supersedes the actual concentration of ALA in the formulation.

Preliminary data obtained during formulation testing (see below for manufacturing details) shows that a 2% thioctic acid concentration formulation of 600 mg reaches a peak plasma level of 2,070 ng 15 minutes after the isomalt lozenge is placed into the mouth. In comparison, an equivalent dose of an orally administered tablet reaches a peak level of 840 ng in 60 minutes. Of particular note is the fact that IV doses within the same dose range and tested by the same methods, reached peak plasma levels of 1,900 ng, since high IV plasma levels are required for maximum benefit. Given this information, and the high peak levels lingual formulations are able to achieve, lingual dosing is it likely to prove therapeutically equivalent to IV dosing and negate the need for invasive needles and expensive medical monitoring when a patient is entered into thioctic acid treatment regimes.

It should be noted that the formulation tests to determine these peak plasma levels were obtained with relatively few subjects and samples. Therefore, there is a level of variability and imprecision in the numbers. The significance of the test is chiefly that our lingual ALA formulation had results that are much closer to the IV plasma levels when compared to the orally administrative tablet (ingested).

One way to regard this is that it would be a significant improvement on existing ALA delivery systems if our lingual formulation achieves peak plasma levels of ALA more similar to those of IV delivery than ingested delivery. For example, considering the ALA plasma levels of 1,900 ng for IV and 840 ng for ingested, if our ALA formulation achieved an ALA plasma level greater than 1,370 ng, then its plasma level would be more similar to that of an IV and less similar to that of ingested ALA administration.

Another way of defining this would be to say that 1,370 ng is 72.11% of 1,900 ng, so it would be a significant improvement on existing ALA delivery systems if our lingual formulation achieves peak plasma levels of ALA within 27.89% of the peak ALA plasma levels of IV delivery.

Therefore, it is somewhat less substantial, but still a modestly significant improvement on existing ALA delivery systems, if our lingual formulation achieves peak plasma levels of ALA within 30% or 35% of the peak ALA plasma levels of IV delivery. It's an even more significant improvement on existing ALA delivery systems if our lingual formulation achieves peak plasma levels of ALA within 25% or 20% of the peak ALA plasma levels attained by IV delivery.

Finally, it's an extraordinary improvement on existing ALA delivery systems if our lingual formulation achieves peak plasma levels of ALA within 15%, 10% or 5% of the peak ALA plasma levels achieved by IV delivery. Because our test results for the lingual formulation of 2,070 ng exceeded the IV results (1,900) by about 8%, we estimate the amount of experimental and measurement error is likely 10% to 15%. Therefore, we believe our results show that our lingual ALA formulation more realistically falls within the range of plus/minus 10% or 15% of that achieved by IV. It's conceivable, however, that more testing will show our lingual formulation achieves peak plasma levels of ALA within any of the above-mentioned percentages of peak ALA plasma levels from IV delivery.

The present invention includes the use of lingual and sublingual delivery systems for thioctic acid, wherein the delivery system is either sucrose or non-sucrose based. The limited-release lingual/sublingual delivery system may be a lozenge, gum, or other release-limiting matrix formulation placed in the patient's mouth and intended to remain in the mouth. The formulation contains a concentration of thioctic acid between 1% and 25% by mass, preferably at a concentration of 1% and 9%, more preferably 1% and 6%, even more preferably 1% and 3% and most preferably at approximately 2% (plus/minus ½% so 1 1/2% and 2 1/2%) by mass.

The formulation's matrix, also known as a diffusion-limiting binding agent, either hard or soft, in the lingual/sublingual formulations may include, but are not limited to: sucrose, isomalt, dextrose(glucose), fructose, lactitol, sorbitol, maltose and chicle.

Inactive ingredient variations in the lingual/sublingual formulations may include, but are not limited to: hydrogenated starch, hydrolysate, gluconic acid, malic acid, lactic acid, sodium lactate, aspartame, glycine, corn syrup, lecithin, cream of tartar, honey, fruit juices, vegetable juices, water, and flavoring oils or alcohols.

Active ingredients in addition to thioctic acid may include (but are not limited to): Selenium, Vitamin E, Vitamin C, Chromium, Potassium, Calcium, gamma-linolenic acid, myoinositol, Vitamin B, Coenzyme Q and various herbal extracts, including, but not limited to, cinnamon, chamomile, marshmallow, anise, *eucalyptus*, peppermint, elder, fennel, licorice, rose hips, sage, and thyme.

Individual lozenges, candies, or other lingual delivery systems are expected to be from 1.0 g to 30.0 g, with thioctic acid dose variations between 10 mg to 600 mg. However, extremely low-dose variations (from 5.0 mg to 10 mg) of thioctic acid are anticipated, such that lozenges for general consumption as a supplement are included in addition to the high-dose formulations intended for specific therapeutic effects. These therapeutic applications may include the treatment of Alzheimer's, diabetic peripheral neuropathies, retinal neuropathies, and other physiological states where thioctic acid therapy is advised or under investigation.

The term dose can be somewhat unclear. It can mean the amount of active ingredient in a single lozenge, tablet or other formulation. It can mean the amount of active ingredient administered in a short period of time, for example taking two aspirin together. Or it could mean the amount of active ingredient administered over a longer period of time such as a day.

The context of use often clarifies the meaning; however, it's worth clarifying our use of it. Unless otherwise specified, we mean dose to refer to a single lozenge, tablet or other unit of formulation. To refer to it specifically, we will use the term Unit-Dose. To refer to two or more lozenges, tablets or other units of formulation, taken together or in relatively rapid sequence, we will use the term Multi-Dose, or for more specific numbers, Double-Dose, Triple-Dose etc.

When using the term dose to refer to a longer period of time, such as a day, where individual unit-doses are taken intermittently, we will use the term Total-Dose or for a particular unit of time, Daily-Dose, Weekly-Dose etc.

The previously mentioned individual lozenges or other lingual delivery systems with thioctic acid dose variations between 10 mg to 600 mg (or 5 mg to 600 mg) refer primarily to a Unit-Dose. Yet the 5 mg or 10 mg to 600 mg dose could also refer to a Multi-Dose scenario. If lozenges, tablets or other units of formulation are quite small, then multiple units could be taken simultaneously.

For example, five, 0.5 g lozenges, each containing 2 mg of ALA, could make a 10 mg ALA Multi-Dose. Or 10, 0.1 g lozenges, each containing 0.5 mg of ALA, could make a 5 mg ALA Multi-Dose.

Therefore, we extend the range for individual lozenges, tablets or other formulations to sizes below 1.0 g if in aggregate they may be reasonably taken as a Multi-Dose that equals 1.0 g or more. Furthermore, we extend the range for individual lozenges, tablets or other formulations to doses of ALA below 5 mg if in aggregate they may be reasonably taken as a Multi-Dose that equals 5 mg or more.

As noted in Table 3 and related discussion, concentrations below 1% are possible and acceptable in terms of preventing thioctic acid burn. However, the issue of having enough thioctic acid to deliver a meaningful dose becomes an issue. It would be reasonable to assume that smaller Unit-Doses, such as 30 mg per day, would still provide some beneficial effects. 30 mg per day spread out over six Unit-Doses (one before and after each meal) would result in a Unit-Dose of 5 mg. Accordingly, even doses as small as 5 mg, to be taken multiple times during the course of the day may provide an effective dose to act as a meaningful maintenance level or prophylactic level of thioctic acid supplementation.

It's worth remembering that smaller Unit-Doses and Total-Doses of ALA (compared to typical ALA doses that are ingested) are possible because the lingual delivery of ALA results in higher peak plasma levels of ALA. Also small Unit-Doses and Total-Doses of ALA could be meaningful, prophylactically or as a treatment, for the mouth, oral tissues or other nearby tissues, because the ALA concentration levels would be expected to be higher in those areas proximal to the ALA release.

For those therapeutic or supplementation purposes in which RLA is believed to be exclusively or primarily effective, the dose might theoretically be cut by 50% for the same effective dose as racemic ALA (or possibly by 25% if SLA interferes with RLA utilization). Accordingly, the low end of the concentration range discussed in this patent should be read to represent values that are multiplied by a factor of 50% (or possibly 25%) when using the possibly more effective thioctic acid enantiomer. The same is true for minimum milligrams of dosing. For example, the 5 mg minimum listed for thioctic acid would be reduced to 2.5 mg (or possibly 1.25 mg). Thus, in cases where the theoretically more active enantiomer is utilized, the minimum concentration range of 1% thioctic acid would actually reflect a minimum concentration range of 0.5% (or 0.25%) when that enantiomer is used alone in the limited release lingual system.

Prior to adding the raw thioctic acid, ensure it is finely powderized with a mortar and pestle. This will make it easier to ensure a homogeneous mixture is obtained.

In a stainless-steel saucepan, add 1.0 cup of sugar (185 g), ½ cup light corn syrup (148 g), and ¼ cup of water (64 g). Using a candy thermometer, heat the mixture up to 300 degrees Fahrenheit, stirring occasionally with a stainless-steel spoon.

As soon as the correct temperature is reached, add ¼ teaspoon (1.3 g) red food coloring, and ½ teaspoon (2.7 g) of cinnamon oil. Mix in completely (avoid stirring too much or candy will become a sugary lump).

Remove from heat and add 10 g of Thioctic acid. Quickly mix in completely, ensuring that mixture becomes homogeneous (lumps or specks will result in a matrix that has a high concentration in small pockets, which can cause problems during administration). Perform this step in a well-ventilated area, since a small fraction of the thioctic acid will sublimate.

To minimize the thioctic acid sublimation, the ALA may be added after cooling down the molten matrix to a temperature below 300 degrees Fahrenheit, such as a temperature (in Fahrenheit) ranging from 280 degrees to 275 degrees, but preferably 275 degrees to 265 degrees, or more preferably 265 degrees to 255 degrees and most preferably 255 degrees to 245 degrees. The lowest temperature that can be used while still providing sufficient time and/or temperature to thoroughly mix the ALA into the matrix is likely the best, unless the ALA sublimation is negligible under a given temperature, say 270 degrees Fahrenheit, and further lowering the matrix temperature before adding ALA would be superfluous.

Immediately pour into hard candy molds that have been lightly coated with vegetable oil (this makes it easier to remove the candy once it has cooled). Let cool completely.

Dust with powdered sugar. This minimizes water absorption during storage and keeps the pieces from sticking together. Store at room temperature away from direct sunlight in sealed baggies or Tupperware containers. For clinical studies, place each lozenge in its own blister pack compartment.

The above recipe yields a 2.5% thioctic acid limited release lingual hard candy lozenge. Exact dosage will depend upon the size of the molds utilized.

Prior to adding the raw thioctic acid, ensure it is finely powderized with a mortar and pestle. This will make it easier to insure a homogeneous mixture is obtained.

In a stainless-steel saucepan add 1.0 cup of Isomalt (185 g), and 4 tablespoons of water (60 g). Using a candy thermometer, heat the mixture up to 300 degrees Fahrenheit, stirring occasionally.

As soon as correct temperature is reached, add ¼ teaspoon (1.3 g) red food coloring, and ½ teaspoon (2.7 g) of cinnamon oil. Mix in completely (avoid stirring too much or candy will become a sugary lump).

Remove from heat and add 6.5 g of Thioctic acid. Quickly mix in completely, ensuring that mixture becomes homogeneous (lumps or specks will result in a matrix that has a high concentration in small pockets, which can cause problems during administration). Perform this step in a well-ventilated area, since a small fraction of the thioctic acid will sublimate.

To minimize the thioctic acid sublimation, the ALA may be added after cooling down the molten matrix to a temperature below 300 degrees (Fahrenheit), such as a temperature (in Fahrenheit) ranging from 280 degrees to 275 degrees, but preferably 275 degrees to 265 degrees, or more preferably 265 degrees to 255 degrees and most preferably 255 degrees to 245 degrees. The lowest temperature that can be used while still providing sufficient time and/or temperature to thoroughly mix the ALA into the matrix is likely the best, unless the ALA sublimation is negligible under a given temperature, say 270 degrees. Fahrenheit, and further lowering the matrix temperature before adding ALA would be superfluous.

Immediately pour into hard candy molds that have been lightly coated with vegetable oil (this makes it easier to remove the candy once it has cooled). Let cool completely.

Store at room temperature away from direct sunlight in sealed baggies, Tupperware containers, or individual blister packs.

The above recipe yields a 2.6% thioctic acid limited release sugar-free lozenge.

Standard Operation Procedures for Lingual Thioctic Acid Release Rate Analysis.

(1) Synopsis of the Lingual Lozenge Dissolution Rate Testing Protocol:

Preliminary in situ testing has revealed an average oral dissolution time of approximately 8-10 minutes for a hard candy sugar matrix ALA (AlphaBon.TM.) lozenge weighing an average of 3.4 grams, comprising 3% thioctic acid. The shape of such lozenge having an approximately 0.28-inch-deep hemispherical, or approximately hemispherical, shape on one side and a flat disc (or polygon) of approximately 1 inch in diameter on the other side or face. To clarify, the lozenge is formed by pouring the molten sugar/ALA matrix into an approximately hemispherical mold, such that the flat disc portion is the top surface of the matrix flowing/pooling to form a flat face). Further in situ testing will be performed to obtain an oral dissolution time that more precisely reflects an average of larger number of subjects.

A discussion of this type of in situ dissolution analysis is described, wherein the release rate can be indirectly determined by the dissolution rate of the lozenge. This type of dissolution testing can be performed ex vivo with artificial *salvia* to determine more consistent dissolution rates than those expected to occur in situ due to physiological differences between subjects. This is specified in the protocol below.

Furthermore, in order to more closely match the average in situ dissolution rate to the conditions used during ex vivo release rate testing the USPC Testing Apparatus to be utilized (Type 2 or Type 4) should be set to a RPM and/or flow rate that allows a similar dissolution time to occur.

To this end, artificial saliva as specified in the detailed section below is utilized as the solvent solution, with a temperature of 35 degrees C. (+/−0.5 degrees C.). Initial flow rate conditions are set at 6.0 nil/min and/or an initial paddle speed of 50 RPM. An ALA formulation is then placed within the relevant testing apparatus and the time for full dissolution to occur is recorded. No samples are obtained during this procedure and all post apparatus solutions are discarded.

The paddle speed and/or flow rate on the testing apparatus is then increased (or decreased) by a factor that reflects the difference in dissolution time between that obtained ex vivo and that seen in situ, such that subsequent runs of the same procedure are repeated until the ex vivo rate of dissolution most closely matches that observed in situ.

However, it is understood that it may not be possible to fully match the dissolution time observed ex vivo due to the limitations of the testing apparatus experimental conditions in matching those actually occurring in vivo (i.e., a lack of tongue mechanical action; factors specific to the artificial saliva solution; oral mucosal removal rates affecting the removal of thioctic acid and/or sucrose; and the presence or absence of enzymes such that diffusion is affected; etc.), in which case the maximum flow rate to be utilized in order to obtain a given release rate should be 15 ml/min. Flow rate speeds above this maximum threshold are expected to distort the concentration of samples obtained and should be avoided. Similarly, the maximum paddle speed is 150 RPM.

Defining In Vivo TEST

If the dissolution times observed ex vivo cannot match those actually occurring in vivo due to any of these limitations then in vivo testing must take precedence.

Also, an in vivo study may be simpler or less expensive and may therefore be a preferred or an initial method to determine if formulation falls within a given range of ALA Dissolution Rates.

To determine if formulation falls within a given range of ALA Dissolution Rates, using an in vivo study, at least 12 subjects each tested three times (three lozenges) must be utilized resulting in 36 results to be averaged. Test procedure is as follows, the lozenge is placed in the mouth for one minute, taken out and weighed (for 30 seconds) and returned to the mouth. This process is then repeated until the lozenge is fully dissolved.

If the results of such a study are challenged by another party and they perform a second in vivo study which finds different results, such that the two studies disagree as to whether such formulation falls within such ALA Dissolution Rate range, then a third study may be performed. Such third study to be performed by a third-party, using twice as many subjects (24), each tested three times, resulting in 72 data points.

The results of any of these in vivo studies must be statistically significant to determine a valid maximum ALA Dissolution Rate for any given formulation.

In the absence of an ex vivo test that can replicate in vivo maximum ALA Dissolution Rates, is more meaningful, more statistically significant, and has a substantially lower standard deviation, such average maximum ALA Dissolution Rate(s) determined by such third study will be considered definitive.

(2) Synopsis of the Lingual Lozenge Release Rate Concentration Testing Protocol(s):

If a USPC Type 2 Paddle Apparatus is utilized it should conform to the following specifications: 25-150 RPM Paddle Speed, 35 degrees C. (+/−0.5 degrees C.).

If a USPC Type 4 How-Through Cell Apparatus is utilized it should conform to the following specifications: 3.0-15.0 ml/min, 35 degrees C. (+/−0.5 degrees C.).

For both apparatus the flow rate and/or paddle speed are set to that determined to be ideal via dissolution testing and the temperature is set to 35 degrees C. (+/−0.5 degrees C.). After equilibrium, an initial sample is taken of the solvent contents of the apparatus and then the ALA formulation is placed in the apparatus and a total of 10 samples are obtained, each at an equal fraction of the total dissolution time.

For example, given a total dissolution time of 10 minutes a blank sample is first obtained, then samples taken at 60 second intervals. At this point the lozenge should be fully dissolved. If the dissolution is 20 minutes, then samples would be taken at 2-minute intervals.

In all cases the sampling time interval should fully encompass the introduction of the ALA formulation into the testing apparatus and its complete dissolution. If more than 10 samples are needed for this process, then more samples should be obtained. Under no condition should samples be taken in less than 30 second intervals, nor more than 3 minutes apart.

**It should be noted that gum based thioctic acid delivery systems will not produce the same release profile as lozenges and tablets utilizing either the Type 2 or Type 4 dissolution apparatus. In the event that these types of formulations are examined a gum specific dissolution devise will be required. Several have recently been patented but wide-spread commercial availability is still lacking. If this system is required, the same artificial saliva should be used as the dissolution medium, at the same temperature, such that only variations in apparatus setup will exist between the new apparatus and the apparatuses discussed in this protocol.

(3) Synopsis of the Thioctic Acid HPLC/ECD Concentration Testing Protocol:

20 µl of each time point sample (resulting from the USPC Type 2 or Type 4 apparatus utilized during the creation of individual release rate samples) are injected into a HPLC which utilizes a mobile phase buffer that is 50% acetonitrile in 0.05 M potassium dihydrogen Phosphate, adjusted to a pH of 2.5 with phosphoric acid.

The HPLC itself should utilize a guard column and a Nucleosil 120-C18 5 µm column, with a flow rate set at 1.0 ml per minute. An electrochemical detector equipped with a glassy carbon electrode set at a potential of +/−1.1 V should be used to quantify the results, with a detection limit of approximately 5 ng/ml. For this protocol, a range of 2.0 µA is advised, with a filter setting of 0.10 Hertz.

To calibrate the HPLC/detector for a given experimental run, FRESH LIPOIC ACID STANDARDS AND SAMPLES MUST BE PREPARED ON THE DAY OF THE EXPERIMENT TO AVOID DRIFT EFFECTS. Under these experimental conditions the retention time for lipoic acid is approximately eight minutes; if pure Acetonitrile is used the exact retention time for any particular equipment setup will be obvious, since following the initial solvent front (which appears early) will be a delayed, distinct lipoic peak (a second, more diluted standard can also be used to more fully calibrate the detector).

If a good quality integrator is used, the reported area under a given peak can be used to evaluate the results. However, if the integrator is unreliable the height of each lipoic peak can be measured by caliper to obtain the same basic results. In either case, to quantify the detector's behavior on a given day standards should be run before, during, and after the samples, and subsequently averaged to obtain an area reported per µg (or mm per µg) value for quantitative analysis.

Specific Details of the ALA Formulation Dissolution Protocol:

| Solvent for AlphaBon ™ Dissolution Rate and Thioctic Acid Release Rate Testing: Artificial Saliva | | |
|---|---|---|
| $KH_2PO_4$ | 2.5 mMol/L | (Monopotassium Phosphate) |
| $Na_2PO_4$ | 2.4 mMol/L | (Disodium Phosphate) |
| $KHCO_3$ | 15.0 mMol/L | (Potassium Bicarbonate) |
| NaCl | 10.0 mMol/L | (Sodium Chloride) |
| $MgCl_2$ | 1.5 mMol/L | (Magnesium Chloride) |
| $CaCl_2$ | 1.5 mMol/L | (Calcium Chloride) |
| Citric Acid | 0.15 mMol/L | |
| (Distilled water to volume) | | | pH adjusted to 6.7 with NaOH or HCl.

A) Determination of Release Rate Acquired by Dissolution Measurements:

In Situ Dissolution Analysis:

When considering the thioctic acid release rate of a solid lozenge (or formulation) several factors will affect the rate of release, the most obvious being the homogeneity of the matrix in which thioctic acid is present, the initial thioctic acid concentration of the matrix, the composition of the matrix itself, and the surface area.

If the matrix is truly homogeneous and the initial concentration of thioctic acid within a lozenge is known at the start of the dissolution process, a determination of mass change over time can be indirectly related to the amount of thioctic acid released within a given time frame. This will hold true for a wide range of possible matrixes provided the lozenge in question is homogeneous. For non-homogenous matrixes direct measurements need to be obtained, such that an indirect determination of the thioctic acid release rate as explained below is believed to be invalid.

By definition the concentration of thioctic acid ([ALA]) in a given lozenge is a measure of the mass of ALA present divided by the total mass of the lozenge {(Mass of ALA)/(Total Mass of the Lozenge)}. Thus, the release of ALA at a given moment is a direct reflection of the change in lozenge mass; see equation #1 below.

$$M^r_{ALA} = (M^i_{Mo2} - M^f_{Lo2}) * \left(\frac{M^i_{ALA}}{M^i_{Lo2}}\right) = (M^i_{Lo2} - M^f_{Lo2}) * \rho = \Delta M * \rho.$$

Equation #1

Therefore, the change in mass at a given point in time can indirectly reflect the amount of ALA lost into solution by the simple application of the concentration value (p) times the mass lost ($\Delta M$).

A determination of the ALA placed in solution over a given unit time is by definition a release rate calculation. Thus, if the change in mass is known, and the time interval is known, it is possible to indirectly determine the release rate by the following formula: {(mass change)×[ALA]}/(time interval).

In this process artificial saliva as specified above is used for the dissolution medium. Although this artificial saliva must be kept at 35 degrees C., as in the Determination of Optimal Dissolution Conditions Protocol listed below, the use of a specific apparatus is not required.

A single lozenge is placed within a containment vessel filled with 100 ml of artificial saliva (35 degrees C.) after its initial mass is determined. The lozenge is then removed at 2-minute intervals with a pair of clean dry forceps, gently blotted dry with a Kimwipe™, and weighed again. This process is continued until the lozenge is too small to accurately handle and/or weigh. A graph of the resulting data can then be used for release rate analysis. The slope of the graph reflects this indirectly determined release rate at any given point during the experiment.

An example of this process is listed below with the data produced from a single in situ oral dissolution trial utilized to provide clarity. The actual dissolution procedure listed in this section is expected to be slightly longer due to differences in temperature and the absence of enzymic factors, thus sampling at one-minute intervals is expected to reflect conditions acquired during the ex-vivo procedure when sampling at two-minute intervals.

TABLE 1

Repeated In situ Oral Dissolution Trial Results (3.43 g Ave, 3% ALA, hard candy sugar lozenge)

| Time (min) | Weight (g) | Change Weight (g) | % ALA | mg ALA lost | mg ALA in Solution | Release Rate (mg/min) |
|---|---|---|---|---|---|---|
| 0 | 3.43 | 0 | 3 | 0 | 0.00 | 0.00 |
| 1 | 3.43 | 0.59 | 3 | 17.63 | 17.63 | 17.63 |
| 2 | 2.84 | 0.67 | 3 | 20.18 | 37.80 | 20.18 |
| 3 | 2.17 | 0.55 | 3 | 16.58 | 54.38 | 16.58 |
| 4 | 1.62 | 0.49 | 3 | 14.70 | 69.08 | 14.70 |
| 5 | 1.13 | 0.46 | 3 | 13.65 | 82.73 | 13.65 |

TABLE 1-continued

Repeated In situ Oral Dissolution Trial Results (3.43 g Ave, 3% ALA, hard candy sugar lozenge)

| Time (min) | Weight (g) | Change Weight (g) | % ALA | mg ALA lost | mg ALA in Solution | Release Rate (mg/min) |
|---|---|---|---|---|---|---|
| 6 | 0.67 | 0.32 | 3 | 9.53 | 92.25 | 9.53 |
| 7 | 0.36 | 0.21 | 3 | 6.15 | 98.40 | 6.15 |
| 8 | 0.15 | 0.10 | 3 | 3.08 | 101.48 | 3.08 |
| 9 | 0.05 | 0.05 | 3 | 1.43 | 102.90 | 1.43 |

In situ Oral Dissolution Trial (3.43 g Ave, 3% ALA, hard candy sugar lozenge) Discussion:

The use of one-minute intervals may introduce spurious data in the collection process due to repeated exposure to air, mechanical friction and the lozenge surface softening (partial dissolution) occurring with saliva remaining on the lozenge surface while it is outside the cavity during the weighing process (about 30 seconds). Additional two-minute and four-minute sampling should be performed to provide context that informs how the issue of weighing the dissolving lozenge every minute impacts the dissolution rate.

It is clear that it is possible to create an indirect analysis of the release rate of thioctic acid from a dissolution procedure that matches expected molecular kinetic models. This indirect method, although lacking modern sophistication and elegance, provides a simple, cost effective, statistically significant, and reasonably meaningful means of comparing various formulations, but would be expected to lack the consistency of the ex vivo methods and/or have less standard deviation.

This mass loss method to determine thioctic acid release, applied to in-vivo dissolution trials as performed in this trial, can be used to provide direct insight into factors affecting individual subjects during the actual use of lingual thioctic acid lozenges. Various measurements of saliva contents during in situ trails could provide insight into levels of salivary mucin release, lipase and amylase release, and other physiological factors.

Those individuals whole display abnormal dissolution rates during in situ trails could be singled out for more extensive investigation into the mechanisms of oral absorption, providing insight into the molecular mechanisms of oral tissue and cellular level thioctic acid uptake and release.

B) Determination of Optimal Dissolution Conditions for Release Rate Analysis:

The USPC Type 2 Paddle Dissolution Testing Apparatus is a standard in the industry but recent reports have shown that this equipment setup can produce erroneous data. For this reason, the Type 4 Flow-Through Apparatus is preferred and also specified in this protocol.

In either instance, artificial saliva (described above) is kept at 35 degrees C. (+/−0.5 degrees C.) and utilized as the dissociation medium.

USPC Type 2 Apparatus

This type of apparatus utilizes a closed vessel and agitates the fluid within it during the dissolution process. The vessel is continuously filled with released product such that the concentrations of the ingredients to be examined rise during the dissolution procedure. For this reason, chemicals that have a low aqueous saturation level can fail to dissolve into solution with a kinetics that matches in situ conditions.

As specified by the 2011 United States Pharmacopeial Convention this type of dissolution apparatus consists of a reaction vessel of inert transparent material, a motor driven stirring element, and a heating element or water bath that maintains the temperature at its specified parameter.

The size of reaction vessel is critical to the data obtained, as is the paddle rotation speed and temperature. The maximum size of the holding vessel for this protocol should be 1 liter (although a smaller chamber would be preferable). The temperature must be maintained at 35 degrees C. (+/−0.5 degrees C.), and an initial Paddle Speed of 50 RPM should be utilized.

A minimal paddle speed of 5 RPM can be utilized during the optimization procedure, and a maximum of 150 RPM. Values outside this range are expected to produce erroneous data since there is less agitation in situ.

Examples of this type of equipment commercially available include, but are not limited to, the Distek 6100 Dissolution System, the Pion μDISS Profiler, and the Agilent Varian VK7025 Dissolution System Apparatus.

USPC Type 4 Apparatus

This type of apparatus utilizes a continuous flow of dissolution medium to record the immediate release rate of a lozenge, such that local concentrations are never able to build up beyond a limited level. This is expected to more closely mimic the conditions seen in situ. For this reason, this apparatus setup is preferred.

As specified by the 2011 United States Pharmacopeial Convention this type of dissolution apparatus consists of a reservoir and pump for the dissolution medium (artificial saliva), a water bath that maintains the dissolution medium at 35 degrees C. (+/−0.5 degrees C.), and a flow through cell.

The pump must maintain a constant flow (+/−5% flow rate) and have a flow profile that is sinusoidal with a pulsation of 120+/−10 pulses per minute (although a pump without pulsation may be used). The rate and pulsation parameters must be consistent and recorded for any analysis to be valid and comparable.

Initial conditions should be such that a flow rate of 6.0 ml/min is set and maintained prior to the introduction of the lozenge into the test chamber. During testing of the Optimal Dissolution Conditions this flow rate is expected to be adjusted between runs until the flow rate that produces a dissolution time equivalent to that seen in situ is produced. The upper maximum for the ideal flow rate should not exceed 15 ml/min, since this condition far exceeds the rate at which saliva is introduced and removed from the buccal cavity.

The transparent and inert flow-through cell is mounted vertically in a water bath with a filter system that prevents the escape of undissolved particles from the top of the cell and has a standard size of 12 or 22.6 mm. The bottom cone is filled with glass beads of 1-mm diameter, with one 5 mm bead positioned at the apex to protect the fluid entry tube from debris. The size of the filter screening system utilized must be recorded and validated for any analysis to be valid and comparable since it can vary from dissolution apparatus to dissolution apparatus.

Example of this type of equipment commercially available include, but are not limited to, the Erweka Flow Through Cell DFZ 720 Open and Closed Offline system, and the Sotax CE 7Smart Semi-Automated UV-Vis On/Off-Line Closed Loop.

Optimization Procedure

Since the goal of this protocol is to find the optimal conditions under which ex vivo dissolution occurs, at this point the use of a dissolution apparatus does not entail the collection of eluted fractions.

For the Type 2 apparatus the dissolution procedure is repeated, adjusting the Paddle RPM on each trial until an in situ comparable rate of dissolution is obtained. This optimal paddle speed will be utilized during release rate analysis using the same equipment setup.

For the Type 4 apparatus the dissolution procedure is repeated, adjusting the flow rate on each trial until an in situ comparable rate of dissolution is obtained. This optimal flow rate will be utilized during release rate analysis using the same equipment setup.

Specific Details of the AlphaBon.TM. Lozenge Release Rate Testing Protocol(s):

| Solvent for AlphaBon ™ Dissolution Rate and Thioctic Acid Release Rate Testing: Artificial Saliva | | |
|---|---|---|
| $KH_2PO_4$ | 2.5 mMol/L | (Monopotassium Phosphate) |
| $Na_2PO_4$ | 2.4 mMol/L | (Disodium Phosphate) |
| $KHCO_3$ | 15.0 mMol/L | (Potassium Bicarbonate) |
| NaCl | 10.0 mMol/L | (Sodium Chloride) |
| $MgCl_2$ | 1.5 mMol/L | (Magnesium Chloride) |
| $CaCl_2$ | 1.5 mMol/L | (Calcium Chloride) |
| Citric Acid | 0.15 mMol/L | |
| (Distilled water to volume) | | |

For either the Type 2 Paddle Dissolution Apparatus or the Type 4 Flow-Through Dissolution Apparatus the dissolution medium is the Artificial Saliva listed above, kept at 35 degrees C. (+/−0.5 degrees C.). For the Type 2 Apparatus, the paddle speed is set to that value determined to be optimal during the dissolution optimization procedure. For the Type 4 flow-through Apparatus the flow rate is set to that value determined to be optimal during the dissolution optimization procedure.

For the Type 2 Paddle Apparatus, 50 μl samples are drawn out of the reaction at 10-20 (ideally 10) specified time points, either via automation or manually. For those samples to be analyzed via automation the system is allowed to determine the concentration of Thioctic acid in each fraction via UV (or other detection methods). For manual analysis each fraction is to be stored in separate aliquots, frozen, and utilized for later thioctic acid concentration analysis via the appropriate detection methodology.

For the Type 2 Flow-Through Apparatus 10-20 (ideally 10) separate 20 μl eluent samples are either immediately analyzed by the system or stored in separate aliquots, frozen, and utilized later for thioctic acid concentration analysis.

The data produced from the Type 2 Apparatus will reflect an increasing concentration of thioctic acid in solution, while the data obtained from the Type 4 Apparatus will reflect how much is being released within a smaller unit of time. Both types of analysis are scientifically sound and have a higher validity than the mathematical dissolution model noted above for use during in situ investigations.

Specific Details of the HPLC/Electrochemical Thioctic Acid Concentration Determination Protocol The samples obtained from the USPC Type 2 or USPC Type 4 apparatus are injected into the HPLC, which utilizes a mobile phase buffer that is 50% Acetonitrile in 0.05 M Potassium Dihydrogen Phosphate, adjusted to a pH of 2.5 with Phosphoric acid. The HPLC itself utilizes Nucleosil 120-C18 5 urn columns, with a flow rate set at 1.0 ml per minute, and a guard column. An electrochemical detector equipped with a glassy carbon electrode set at a potential of +/−1.1 V should be used to quantify the results.

For this protocol, calibration controls will be linear within the 100 ng to 5 ug range, and so 257 ng concentrations of lipoic acid in acetonitrile should be used for each daily run. These calibration standards MUST be freshly prepared at the beginning of each HPLC analysis run.

The height of each lipoic peak is measured and recorded for each time point. The height of calibration controls for each daily run are then averaged, and ng per mm values obtained from these averages. These values are then used to compute lipoic acid concentrations in plasma for each time point. Data is subsequently adjusted to normalize any variations in dosages and to reflect dilutional effects (i.e., multiplied by two).

For each formulation the maximum peak is determined, and the total absorbed lipoic acid is estimated from an area under the concentration time curve (AUC) analysis of the kinetic curves. For the most part, no consideration should be given to racemic compositions and differences.

20 µl HPLC Sample Analysis

Turn on ECD and HPLC and allow system to equilibrate.

Inject 2.0 µg/ml standard and allow system to fully return to baseline.

Repeat 2.0 µg/ml standard injection (checks that HPLC system is stable).

Inject Sample and allow system to return to baseline. (repeat steps 3 & 4 for each sample to be analyzed).

Inject 2.0 µg/ml standard and allow system to fully return to baseline.

Average the areas (or heights) for the standard and divide by 2.0 to produce an area per µg (or mm per µg) value.

Divide the sample's reported area (or height) by the value produced in step (6) above to compute the sample's actual lipoic value in µg/ml.

HPLC Testing Specifics:

a) HPLC System Preparation:

Make sure that the HPLC has no leaks, and that both in-line filters and guard columns are fresh enough to allow a good flow. To be sure this is so, check the PSI on the pump, which should be about 2.5 K at the start of a run (before samples clog the system).

If the system has not been used for several days, it should be running non-buffered mobile phase. Therefore, shutting down the pump momentarily, switch the Mobile phase on line (A) from a Non-Buffered Mobile Phase bottle to a Buffered Mobile Phase bottle.

If the system has been used within the last day, it should already be running buffered mobile phase.

Ideally, the ECD and HPLC should be switched to Buffered mobile phase and allowed to run at 0.3 ml/min overnight prior to actual use.

Either way, the HPLC should run Buffered Mobile phase for at least three hours prior to actually performing sample injections, and be set to a flow rate of 1.0 ml/min prior to and during injections.

b) ECD System Preparation:

Polish the cell contacts within the top cabinet of the ECD.

Replace the reference electrode with a re-charged one that has been stored in a high concentration of NaCl for at least three days.

With the ECD set to standby, turn the system to an AppE of 1.001, a range of 1.0, and a filter of 0.10 or 0.15.

Ideally, the ECD and HPLC should be switched to Buffered mobile phase and allowed to run at 0.3 ml/min overnight prior to actual use. If this is not possible, at least three hours must pass if solvent is changed or detector components have been altered.

In either case, let the system run at the flow rate used for injections (1.0 ml/min) for 15-20 minutes before using it, especially if the flow rate or sensitivity range has been changed (either right before, or during sample injections).

If the detector must be re-set (i.e., with a new reference electrode and/or cell polishing), at least three hours must pass before subsequent use.

c) HPLC Sample Injection Procedures:

With the HPLC and ECD at full equilibrium (see above), 50 ul are drawn with a calibrated syringe from that day's 260 ng standard, and about 40 ul are injected into the manual injector while it is the "LOAD" position (DO NOT TRY TO DELIVER ALL 50 ul's, since this can introduce an air bubble into the system). Given that the system uses a 20 ul loop, this size sample insures uniform loading and clearing of trace amounts from the needle injector port).

Turn the Manual Injector to "Inject", and hit the Marker switch on the front of the ECD.

This insures that a dash is created on the chart, so that it is possible to determine which of the following peaks is actually that belonging to the ALA in the sample.

Flush the syringe itself 4-6 times with pure acetonitrile to remove excess ALA and other debris.

When the chart moves far enough to make it possible to connect a line to the hash mark, record on the chart what has been injected and enclose it in a rectangular box.

At a specific time, from 5-8 minutes post injection (depending upon the PSI, room temperature, and other factors), the ALA peak with show up on the chart. Label that peak with a note enclosed in a balloon shaped box (in this case, as the 260 ng standard).

Once the ALA peak has passed and the chart is at baseline again, reset the injector to "Load" and repeat the above procedure with a second 260 ng standard.

Following the initial two injections of 260 ng standards, sample injections can begin.

Samples should be injected as per the standards, but in a random tandem order. In other words, all samples for a given time point should be processed together, but the time points themselves should be randomized (see example below).

The syringe should be well cleaned between every injection, and a given time point series should be followed by a single 260 ng standard injection (see example below) to test ECD integrity and insure sensitivity decline is accounted for during analysis.

In the event that detector sensitivity declines too greatly, the system should be shut down and the cause of the problem addressed before further sampling is done. In the event of this occurrence, all remaining samples should be quickly returned to the freezer for subsequent use.

d) HPLC System Shut Down Procedures:

Unless the HPLC's PSI is still low, the inline filters should be changed at the end of a day's sample runs. Before doing this, remember to put the ECD in standby and shut down the pump.

Following filter (and perhaps guard column) changing, the HPLC should be turned back on and allowed to clean itself out for at least 15 minutes at 1.0 ml/min.

If the ECD has lost sensitivity, replace reference electrode and polish cell (see above) before turning HPLC back on.

If the system is to be used within the next 24 hours, keep buffered mobile phase running, but turn flow rate down to 0.3 ml/min.

If the system is NOT to be used for several days, then switch to non-buffered mobile phase and let it run through the system for at least 15-30 minutes at a 1.0 ml/min flow rate before switching to 0.3 ml/min flow rate.

Once the system is running "clean", place outlet line into inlet bottle (so fluid returns to the same bottle it is leaving).

Ideally, a separate bottle buffered mobile phase should be used for overnight re-circulation than that used for actual HPLC analysis, in order to minimize the chances of contamination. In this case, one bottle of buffered mobile phase would be used during the HPLC, while another would be used to keep the system ready for use. Thus, the non-buffered mobile phase should only be used if the system is going to be put in standby, for use several days later.

HPLC Data Analysis:

a) ALA Manual Peak Height Measurement:

Using a straight edge, draw a line that connects the two ends of the baseline below the given peak.

Using the caliper set in mm (not inches), and being sure to re-zero the gauge before each measurement, measure the distance from the drawn baseline to the top of the peak and record it next to the label for that peak.

Note: If a given peak goes off the chart, that sample should be re-run at a higher range (say 5.0 or 10.0 rather than 1.0).

b) ALA mm to ng/ml Conversions:

Using the 260 ng standards as true values, take the average of two or more values and divide that average by 260. This will give you the mining value for any given peak's mm height.

Under the conditions outlined above, there will be two 260 ng values at the start of the run, and then one immediately after the first round of samples. These samples would utilize this mm/ng factor to determine how much ALA is present. The STD error for these sample points is the STD error in this first average.

Subsequent samples will be bracketed by two 260 ng standards. These standards are averaged with the previous average, and again the STD in this new average is assumed to be the STD in the samples that use this new average to compute mining values.

HPLC Liquids and Standards Preparation Protocols:

a) Buffered Mobile Phase Recipe: (Makes 2.0 Liters)

Label a clean 2.0 liter bottle "BUFFERED MOBILE PHASE—50% ACN".

Using a clean flask, add 1.0 liter of pure, distilled water.

Measure out 13.610 grams of Na2HPO3 (Disodium Phosphate), recording actual mass, and add to the 1.0 liter of water.

Add phosphoric acid drop-wise until pH is about 3.0, testing after every few drops.

Add 1.0 liter of HPLC grade acetonitrile to the 1.0 liter of pH balanced buffer.

Filter the resulting 2.0 liters of Mobile phase to remove excess salt and micro-particles.

Pour the filtered Mobile phase into the labeled bottle and seal.

Record the date, and who made the Mobile phase, on the side of the bottle and leave for HPLC technician.

b) Non-Buffered Mobile Phase Recipe: (Makes 2.0 Liters)

Label a clean 2.0 liter bottle "RECIRCULATE MOBILE PHASE—50% ACN".

Using a clean flask, add 1.0 liter of pure, distilled water.

Add 1.0 liter of HPLC grade acetonitrile to the 1.0 liter of pure water.

Filter the resulting 2.0 liters of Mobile phase to remove micro-particles.

Pour the filtered Mobile phase into the labeled bottle and seal.

Record the date and who made the Mobile phase on the side of the bottle, and leave for HPLC technician.

c) Creation of 2.6 µg ALA Calibration Standard Solution:

Place 200 mg of ALA in 30 ml Acetonitrile. *(this solution is 6.6 mg/ml)

Using a clean stir bar, mix until fully dissolved.

Place 24.5 ml of pure Acetonitrile in a large centrifuge tube.

Add 0.5 ml of 6.6 mg/ml ALA stock solution and mix. *(this solution is 0.132 mg/ml ALA)

Place 24.5 ml of pure Acetonitrile in another centrifuge tube.

Add 0.5 ml of 0.13 mg/ml ALA solution and mix. *(this solution is 2.64 µg/ml ALA). *(This is the standard from which 20 µl samples are drawn).

d) 260 ng ALA Sample Standard Preparation:

Get 1 small (5.0 ml), and three large (50.0), fresh centrifuge tubes (with caps).

Write the date on each tube.

Label the small (5.0 ml) tube "Stock—0.033 g/ml ALA".

Place 4.0 ml of acetonitrile into this tube.

Weigh out 0.133 grams of ALA, recording actual mass, and add to the acetonitrile containing tube.

Cap and mix this solution until it becomes homogeneous.

Label one of the large (50 ml) centrifuge tubes "1-1.0 mg/ml ALA".

Add 49.0 ml of acetonitrile to this tube.

Remove 1.0 ml of liquid from the first tube (0.033 g/ml), and add to this 49.0 ml of acetonitrile.

Cap both tubes, and mix the second tube for several minutes.

Label a second large (50 ml) centrifuge tube "2-10 ug/ml ALA".

Add 49.5 ml of acetonitrile to this second tube.

Remove 0.5 ml of liquid from the tube labeled "1-1.0 mg/ml ALA" and add to this 49.5 ml of acetonitrile.

Cap both tubes, and mix the new tube for several minutes.

Set aside the "1-1.0 mg/ml ALA" tube.

Label the third large (50 ml) centrifuge tube "3-260 ng/ml ALA".

Add 48.7 ml of acetonitrile to this large tube.

Remove 1.3 ml of liquid from the "2-10 ug/ml ALA" tube and add to this 48.7 ml of acetonitrile.

Cap both tubes, and mix the new tube for several minutes.

Set aside the "2-10 ug/ml ALA" tube.

The new tube, "3-260 ng/ml ALA" is the standard that is utilized on that given day.

The original tube, "Stock—0.033 g/ml", can be used for standard creation on other days within 1 week of its creation, but all the other tubes (1-3) are only good for the day they are made and should be discarded at the end of the day.

CONCLUSION

When the diffusion-limiting binding agent is used as a lingual/sublingual delivery system, it provides a uniquely and synergistically effective method of delivering thioctic acid to a patient's bloodstream in supplemental and therapeutic doses.

The invention claimed is:

1. A method of increasing the concentration of alpha-lipoic acid in an individual comprising (a) delivering a dissolvable, compressed tablet, not characterizable as a hard candy lozenge, formed by a method comprising compressing two or more tablet ingredients without the application of heat other than heat naturally occurring due to the compression of the tablet ingredients, and comprising alpha-lipoic acid in a concentration of 7.5-27%, to the mouth of the individual, such that dissolving the dissolvable, compressed tablet in the mouth results in a sustained release profile comprising a first peak release rate and a second peak release rate of the alpha-lipoic acid from the dissolvable, compressed tablet, and (b) maintaining the dissolvable, compressed tablet in the mouth of the individual until the dissolvable, compressed tablet is fully dissolved, wherein the second peak release rate does not exceed the first peak release rate, and wherein at least 50% of the individuals in a population of typical individuals administered the dissolvable, compressed tablet do not experience a burning sensation which causes such individuals to be unable to maintain the dissolvable, compressed tablet in their mouth until the dissolvable, compressed tablet is fully dissolved.

2. The method of claim 1, wherein the alpha-lipoic acid is racemic ALA.

3. The method of claim 1, wherein administration of the dissolvable, compressed tablet results in the blood concentration of alpha-lipoic acid in the individual reaching at least 65% of the concentration achieved by intravenous administration of the same amount of alpha-lipoic acid.

4. The method of claim 1, wherein the alpha-lipoic acid in the dissolvable, compressed tablet is in a concentration of 9-27%, and the average response in a population of test subjects is that the dissolvable, compressed tablet is acceptable for daily use despite any irritation incurred in dissolving the tablet in the mouth.

5. The method of claim 2, wherein the alpha-lipoic acid in the dissolvable, compressed tablet is in a concentration of 9-27%, and the average response in a population of test subjects is that the dissolvable, compressed tablet is acceptable for daily use despite any irritation incurred in dissolving the tablet in the mouth.

6. The method of claim 3, wherein administration of the compressed tablet results in the blood concentration of alpha-lipoic acid in the individual reaching at least 85% of the concentration achieved by intravenous administration of the same amount of alpha-lipoic acid.

7. The method of claim 4, wherein the population of test subjects comprises testing of at least 12 subjects.

8. The method of claim 5, wherein the population of test subjects comprises testing of at least 12 test subjects.

9. The method of claim 1, wherein the dissolvable, compressed tablet has a peak alpha-lipoic acid release rate that is at least 40 mg/minute.

10. The method of claim 9, wherein the dissolvable, compressed tablet has a peak alpha-lipoic acid release rate that is at least 60 mg/minute.

11. The method of claim 1, wherein the individual is an individual who would otherwise experience intolerable burning caused by the alpha-lipoic acid if the same concentration of alpha-lipoic acid were administered to the individual in the form of a hard candy lozenge.

12. The method of claim 1, wherein the individual is an average user for whom any burning sensation experienced by allowing the dissolvable, compressed tablet to completely dissolve in the individual's mouth is found to be tolerable when the dissolvable, compressed tablet is used for everyday prophylactic or supplemental use to promote health.

13. The method of claim 1, wherein administration of the dissolvable, compressed tablet results in the blood concentration of alpha-lipoic acid in the individual reaching a higher level than the blood concentration of alpha-lipoic acid achieved by the administration of the same amount of alpha-lipoic acid administered by ingestion.

* * * * *